United States Patent

Hogendijk

[19]

[11] Patent Number: 6,080,175
[45] Date of Patent: Jun. 27, 2000

[54] SURGICAL CUTTING INSTRUMENT AND METHOD OF USE

[75] Inventor: Michael Hogendijk, Palo Alto, Calif.

[73] Assignee: Corvascular, Inc., Palo Alto, Calif.

[21] Appl. No.: 09/124,534

[22] Filed: Jul. 29, 1998

[51] Int. Cl.[7] ............................................. A61B 17/34
[52] U.S. Cl. ........................................ 606/185; 606/167
[58] Field of Search ..................... 606/184, 185, 606/190, 167; 604/264

[56] References Cited

U.S. PATENT DOCUMENTS

| | | |
|---|---|---|
| 3,844,272 | 10/1974 | Banko ................................ 128/2 |
| 4,203,444 | 5/1980 | Bonnell et al. . |
| 4,596,552 | 6/1986 | DeVries . |
| 4,721,116 | 1/1988 | Schintgen et al. ................ 128/751 |
| 5,013,296 | 5/1991 | Buckberg et al. . |
| 5,037,379 | 8/1991 | Clayman et al. . |
| 5,074,872 | 12/1991 | Brown et al. ..................... 606/182 |
| 5,106,364 | 4/1992 | Hayafuji et al. . |
| 5,129,913 | 7/1992 | Ruppert ............................. 606/184 |
| 5,151,087 | 9/1992 | Jonkman . |
| 5,275,609 | 1/1994 | Pingleton et al. . |
| 5,290,303 | 3/1994 | Pingleton et al. . |
| 5,336,176 | 8/1994 | Yoon ................................. 606/185 |
| 5,368,606 | 11/1994 | Marlow et al. . |
| 5,372,588 | 12/1994 | Farley et al. ...................... 606/185 |
| 5,387,215 | 2/1995 | Fisher . |
| 5,423,840 | 6/1995 | Casebeer et al. ................. 606/166 |
| 5,423,844 | 6/1995 | Miller . |
| 5,431,173 | 7/1995 | Chin et al. . |
| 5,456,684 | 10/1995 | Schmidt et al. . |
| 5,501,698 | 3/1996 | Roth et al. . |
| 5,527,332 | 6/1996 | Clement . |
| 5,540,693 | 7/1996 | Fisher . |
| 5,569,243 | 10/1996 | Kortenbach et al. .............. 606/46 |
| 5,577,517 | 11/1996 | Bonutti . |
| 5,599,347 | 2/1997 | Hart et al. ......................... 606/42 |
| 5,611,803 | 3/1997 | Heaven et al. . |
| 5,618,296 | 4/1997 | Sorensen et al. . |
| 5,645,556 | 7/1997 | Yoon ................................. 606/185 |
| 5,669,876 | 9/1997 | Schechter et al. . |
| 5,676,670 | 10/1997 | Kim . |
| 5,685,840 | 11/1997 | Schechter et al. . |
| 5,693,011 | 12/1997 | Onik . |
| 5,695,511 | 12/1997 | Cano et al. . |
| 5,725,544 | 3/1998 | Rygaard . |
| 5,730,752 | 3/1998 | Alden et al. . |
| 5,857,999 | 1/1999 | Quick et al. ...................... 604/107 |

*Primary Examiner*—Michael Buiz
*Assistant Examiner*—Jonathan D. Goldberg
*Attorney, Agent, or Firm*—Morrison & Foerster LLP

[57] ABSTRACT

A surgical cutting instrument adapted for percutaneous insertion into a body cavity to facilitate a minimally invasive surgical procedure. The surgical cutting instrument includes a shaft having a proximal end, an open distal end, and an axial lumen therebetween. An inlet opening may be fluidly coupled to the lumen at a proximal end of the shaft, for connection to a vacuum source for creating a suction force sufficient to retain the distal end of the shaft adjacent to a surface of a body structure within the body cavity. A cutting element is disposed within the lumen of the shaft near the distal end of the shaft, and is operable to cut the body structure without removing any substantial portion of the body structure when the shaft is held adjacent to the surface of the body structure.

47 Claims, 13 Drawing Sheets

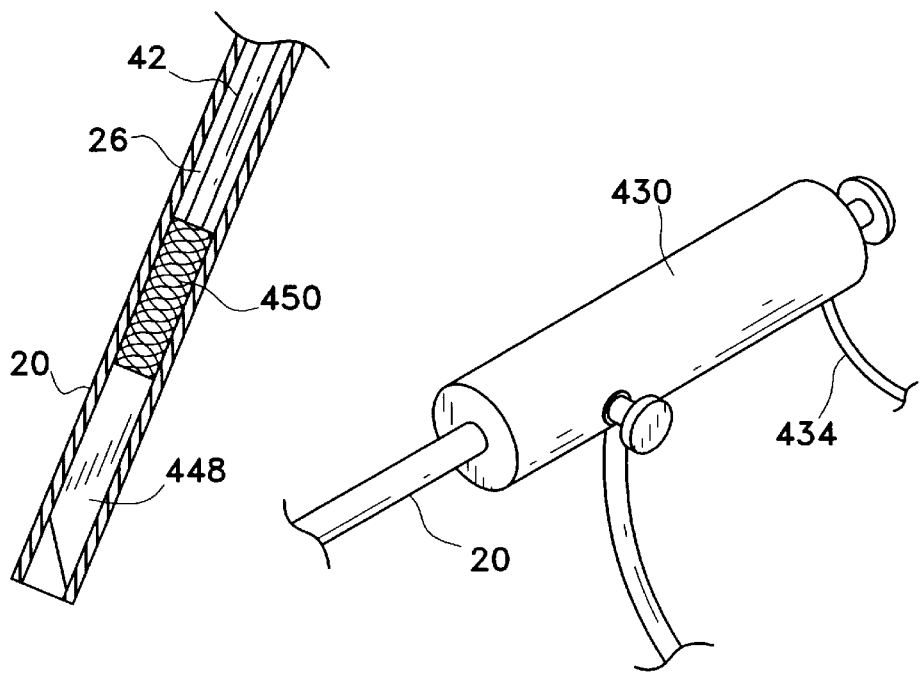
Fig. 14A
Fig. 14B
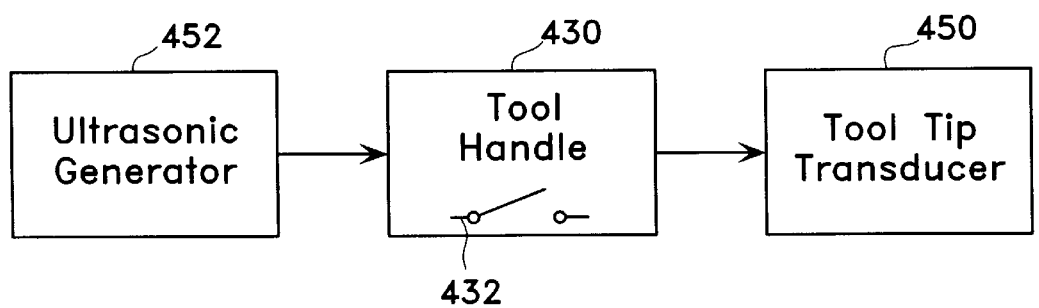
Fig. 15

SURGICAL CUTTING INSTRUMENT AND METHOD OF USE

TECHNICAL FIELD

The present invention relates generally to instruments for performing minimally invasive surgery, such as minimally invasive cardiac bypass surgery, and more specifically to a surgical cutting instrument adapted for percutaneous insertion into a body cavity of a patient and useful for cutting a body structure within the body cavity, such as a thoracic organ or an artery, vein, or other vessel, without substantially removing any portion of the body structure.

BACKGROUND ART

Minimally invasive surgical techniques have revolutionized cardiac surgery. Minimally invasive cardiac surgery enjoys the advantages of reduced morbidity, quicker recovery times, and improved cosmesis over conventional open-chest cardiac surgery in which the surgeon "cracks" open a patient's chest by sawing through the breastbone or sternum. Recent advances in endoscopic instruments and percutaneous access to a patient's thoracic cavity have made minimally invasive surgery possible. Reduction in morbidity, lower cost, and reduced trauma has made minimally invasive surgery desirable.

One approach to minimally invasive cardiac surgery is an endoscopic procedure in which access to the heart is gained through several small openings, or ports, in the chest wall of a patient. The endoscopic method allows surgeons to stop the heart without cracking the chest by utilizing a series of internal catheters to stop blood flow through the aorta and to administer cardioplegia solution to facilitate stopping the heart. The endoscopic approach utilizes groin cannulation to establish cardiopulmonary bypass (CPB) which takes over the function of the heart and lungs by circulating oxygenated blood throughout the body. After CPB is started, an intraaortic balloon catheter that functions as an internal aortic clamp by means of an expandable balloon at its distal end is used to occlude blood flow in the ascending aorta from within. A full description of an example of one preferred endoscopic technique is found in U.S. Pat. No. 5,452,733, the complete disclosure of which is incorporated by reference herein. A primary drawback of endoscopic cardiac surgery procedures, however, is that such procedures do not avoid the damaging effects of CPB. CPB has been shown to be the cause of many of the complications that have been reported in conventional coronary artery bypass graft (CABG) procedures, such as stroke. The period of cardiopulmonary bypass should be minimized, if not avoided altogether, to reduce patient morbidity.

An approach to minimally invasive cardiac surgery that avoids CPB is minimally invasive direct coronary artery bypass grafting (MIDCAB) on a beating heart. Using this method, the heart typically is accessed through a mini-thoracotomy (i.e., a 6 to 8 cm incision in the patient's chest) which also avoids the sternal splitting incision of conventional cardiac surgery. The anastomosis procedure is then performed under direct vision on the beating heart. However, there are many obstacles to precise coronary anastomosis during MIDCAB. In particular, the constant translational motion of the heart and bleeding from the opening in the coronary artery hinder precise suture placement in the often tiny coronary vessel.

In response to problems associated with the above-described minimally invasive surgical techniques, a new surgical platform known as the TRANSARREST™ platform has been developed to minimize the cardiac motion of the beating heart. The TRANSARREST™ platform employs a novel pharmaceutical approach to stabilizing the heart. This revolutionary pharmaceutical approach to cardiac stabilization is fully described in co-pending provisional patent application for Compositions, Apparatus and Methods For Facilitating Surgical Procedures, Ser. No. 60/055,127, filed Aug. 8, 1997 and invented by Francis G. Duhaylongsod, M.D, the entire contents of which are expressly incorporated by reference herein. As described therein, pharmaceutical compositions, devices, and methods are provided which are useful for medical and surgical procedures which require precise control of cardiac contraction, such as minimally invasive CABG procedures. Generally, the TRANSARREST™ platform involves the intracoronary administration of a novel drug composition which provides for precise heart rate and rhythm control management while maintaining the ability of the heart to be electrically paced. Electrical pacing wires are connected to the right ventricle and/or left ventricle and/or atria and are used to pace the heart using a novel foot-actuated pacer control system to maintain the patient's blood circulation during the periods in which the surgeon is temporarily not performing the surgical procedure. Thus, for example, in a CABG procedure, the surgeon can control the pacing of the heart with a convenient foot pedal and can controllably stop the heart as sutures are placed in the vessel walls. The pharmaceutical compositions, devices and methods for drug delivery, and systems for pacing the heart, give a surgeon complete control of the beating heart.

The TRANSARREST™ procedure described above can be used to facilitate any surgical procedure within the thoracic cavity or other body cavity which requires intermittent stoppage of the heart or elimination of movements caused by pulsatile blood flow, whether access is gained to the body cavity via a partial or median sternotomy incision, via a mini-thoracotomy incision, or via one or more small incisions or ports in the chest wall. Ideally, the least invasive manner in which to perform the surgical procedure is through small incisions and/or trocar sleeves disposed in the chest wall, which avoids the morbidity and reduces the pain and trauma associated with open surgical procedures. However, in order to perform the TRANSARREST™ surgical procedure, or any other thoracoscopic procedure least invasively, new highly specialized microsurgical instruments and methodologies are required since the minimally invasive cardiac surgery field is relatively new and evolving. In particular, a microsurgical cutting instrument is needed which preferably can be inserted into a body cavity percutaneously via a small port incision, accurately manipulated from outside the body cavity, and adapted to be used for extremely small scale microsurgical cutting procedures within the body cavity. Preferably, the surgical cutting tool should be adapted to perform the fine incisions required for an arteriotomy, aortotomy, atriotomy or other similar incision in the tiny coronary vessels, other great vessels of the heart, or peripheral vessels, to facilitate coronary anastomosis, for example. The instrument preferably should be used in concert with remote viewing devices, such as an endoscope, thoracoscope, and the like that can be inserted through small incisions and used to view the operative site.

Over the past decade, cutting instruments have been developed to facilitate minimally invasive surgical techniques, particularly in the areas of arthroscopy, laproscopy, pelviscopy, and the like. Such procedures typically target large internal body structures and involve both the excision and removal of large masses of body tissue during the surgery. The cutters used for such procedures typically employ some form of rotary or linearly reciprocating device to cut the tissue and vacuum means to remove the tissue from the body cavity, such as in arthroscopic joint procedures. An example of a rotary device used for tissue excision and removal is U.S. Pat. No. 4,203,444 to Bonnell et al. The Bonnell device utilizes an outer tube having a side-facing, axially extending cutting port and an internal rotary blade. A vacuum conduit draws the tissue to be sheared into the cutting port while the rotary blade is driven in shearing relation to the external tube. The vacuum further draws the cut body tissue through a tube lateral to the handle and out of a side port of the instrument for disposal. An example of a linearly reciprocating tissue cutter for excising and removing body tissue during surgery is found in U.S. Pat. No. 5,527,332 to Clement. These cutting instruments, and other similar morcellator-type instruments used for minimally invasive arthroscopic and laproscopic procedures, lack the high degree of precision and control necessary for microsurgical cutting procedures on very small body structures, such as the tiny coronary vessels, and particularly are not well suited for cutting procedures in which it is damaging to remove any substantial portion of the body structure.

Instruments have been developed to facilitate thoracoscopic CABG and other minimally-invasive microsurgical cutting procedures on small body structures within the thoracic cavity, such as the microsurgical devices described in U.S. Pat. No. 5,501,698. The endoscopic surgical cutting instruments described therein have an end-effector for cutting tissue in the form of forward or rearward-cutting scissors disposed at the distal end of an extended shaft. The scissors are manipulated from the proximal end of the shaft outside the body cavity to make small incisions in a target coronary artery or other vessel or small body structure, which is typically several inches away from the actuating mechanism at the proximal end of the device. The drawback of such cutting devices is that it is difficult to precisely control the cutting motion of the distal end-effector. Because the vessel is several inches away from the proximal end of the device, any slight movement at the proximal end of the tool will cause the distal, cutting end of the tool to jump or bounce, i.e., move in an exaggerated manner. Such surgical cutting tools provide no mechanism to stabilize the distal, cutting end of the tool to precisely control the location, depth, and length of the cut in the target vessel or other small body structure.

A need therefore exists for a surgical cutting instrument and method to facilitate the performance of minimally-invasive microsurgical procedures, and particularly, the performance of thoracoscopic CABG and other procedures on the heart and coronary and/or peripheral vessels. The surgical cutting instrument preferably should be adapted to be percutaneously inserted into a body cavity, such as the thoracic cavity, through small incisions or trocar sleeves in the chest wall, and simply, quickly, and precisely manipulated from outside the body cavity to make very fine incisions in the coronary vessels (or other small body structure) without substantially removing any portion of the vessels. The surgical cutting instrument must have a length sufficient to reach the heart and other thoracic organs and vessels from various percutaneous access points. Preferably, the surgical cutting instrument should have the capability to stabilize the distal end of the instrument to minimize any unwanted movements of the device during the actual cutting operation.

SUMMARY OF THE INVENTION

The above mentioned drawbacks of the prior art are overcome by the provision of a surgical cutting instrument ideally suited for minimally invasive surgery, and particularly to minimally invasive CABG procedures on the heart and great vessels. Although features of the present invention have particular utility for minimally invasive cardiac surgery procedures, where access is gained to the heart via small ports in the chest wall, the instruments described herein can be advantageously used in any other cardiac or other surgical procedures, such as conventional open-chest procedures. According to one aspect of the present invention, a surgical cutting instrument is provided which includes an elongate shaft having a proximal end, a distal end adapted for percutaneous insertion into a body cavity within a patient, and an axial lumen therebetween. A stabilizing element is associated with the distal end of the shaft, and a cutting element disposed within the lumen of the shaft near the distal end. The cutting element and the shaft are relatively moveable between a first position and a second cutting position. The cutting element is adapted to cut a body structure within the body cavity when the cutting element and the shaft are in the second cutting position. The stabilizing element, upon actuation, is adapted to maintain the body structure in a stable position adjacent the distal end of the shaft.

Preferably, the distal end of the shaft has an outside diameter of less than about 5 mm, and the cutting element comprises at least one blade which has a substantially straight cutting edge. Preferably, the cutting edge is displaced at an angle of between about 15 to 30 degrees relative to a vertical axis through the blade.

The cutting element may be movably disposed within the lumen of the shaft. In this case, the cutting element is fixed to an actuator push rod located within the lumen of the shaft, and connected to an actuator, preferably an actuator button, at a proximal end thereof.

Alternatively, the shaft may be movably disposed with respect to the cutting element. In this case, the shaft is slidably mounted to a handle of the cutting instrument. An anchor, preferably a rigid rod coaxially disposed within the shaft, fixes the cutting element to the handle. An actuator member mounted to the shaft, and biased by a biasing element, preferably a spring, may be actuated to slide the shaft between first and second positions with respect to the cutting element.

The cutting element may include at least one blade which is operably coupled to a source of ultrasonic energy. The stabilizing element preferably comprises a vacuum line fluidly coupled to the lumen of the shaft. The vacuum line is adapted to connect to a vacuum source to effect a suction force at the distal end of the shaft. A control mechanism is provided to selectively block flow between the vacuum source and the lumen. The control mechanism may include a slide valve, an on/off button, or other equivalent mechanism for selectively closing and opening the vacuum pathway.

Alternatively, the stabilizing element may include a gripper assembly associated with the distal end of the shaft and configured to grip a portion of the body structure.

Additionally or alternatively, at least one electrode may be disposed near the distal end of the shaft to effect or enhance cutting. An electrode may be operatively coupled to the cutting element, preferably substantially colinearly coupled to the cutting edge. A connector is associated with the proximal end of the shaft for electrically coupling the electrode(s) to an electrosurgical power supply.

An irrigation port may be fluidly coupled to the lumen of the shaft and connectable to a source of irrigation fluid for clearing debris away from the body structure.

According to a further aspect of the invention, a method for cutting a body structure within a body cavity without removing any substantial portion of the body structure is provided, which includes percutaneously introducing a distal end of a surgical cutting instrument through a percutaneous opening in the body cavity; retaining the distal end relatively immobile with respect to a surface of the body structure; and manipulating the surgical instrument from outside the body cavity to position a cutting element of the surgical cutting instrument in contact with the body structure to cut the body structure.

Preferably, the retention is accomplished by applying suction through the distal end of the instrument. The manipulation may include actuating an actuator body, externally of the percutaneous opening, to move a cutting element disposed near a distal end of the shaft from a first position to a second, cutting position. The manipulation may include actuating the shaft to move from a first position, in which the shaft substantially covers the cutting element, to a second position in which at least a portion of the cutting element is exposed for cutting the body structure.

Additionally, radiofrequency energy may be applied to the body structure to facilitate making a cut in the body structure. Ultrasonic energy may be applied to the cutting element to effect or enhance cutting.

BRIEF DESCRIPTION OF THE DRAWINGS

FIG. 14A is a schematic view of the distal portion of another embodiment of the surgical cutting instrument according to the present invention which employs an ultrasonic transducer.

FIG. 14B is a partial perspective view of the embodiment of FIG. 14A, which shows the proximal portion of the embodiment.

FIG. 15 is a block diagram showing an interconnection of elements in the embodiment of FIGS. 14A–B.

DETAILED DESCRIPTION

The devices and methods of the present invention for cutting a body structure such as a blood vessel will now be described in detail. The surgical cutting instruments and methods of the present invention are particularly well-suited for thoracoscopic CABG procedures, in particular for making precise arteriotomy incisions in a diseased coronary vessel, such as a stenosed left anterior descending artery downstream from the stenosis. Although the present invention is particularly well-suited to minimally invasive thoracoscopic procedures, it is to be understood that the invention can be used in any procedure where a fine incision needs to be made with precision and control in any internal body structure, including conventional, open procedures, minithoracotomy procedures, and pure endoscopic minimally invasive procedures. For example, the instrument of the present invention may be used for MIDCAB procedures on a beating heart wherein the retention mechanism described below can be used to minimize the motion of the heart to facilitate the cutting procedure.

Figure 1:
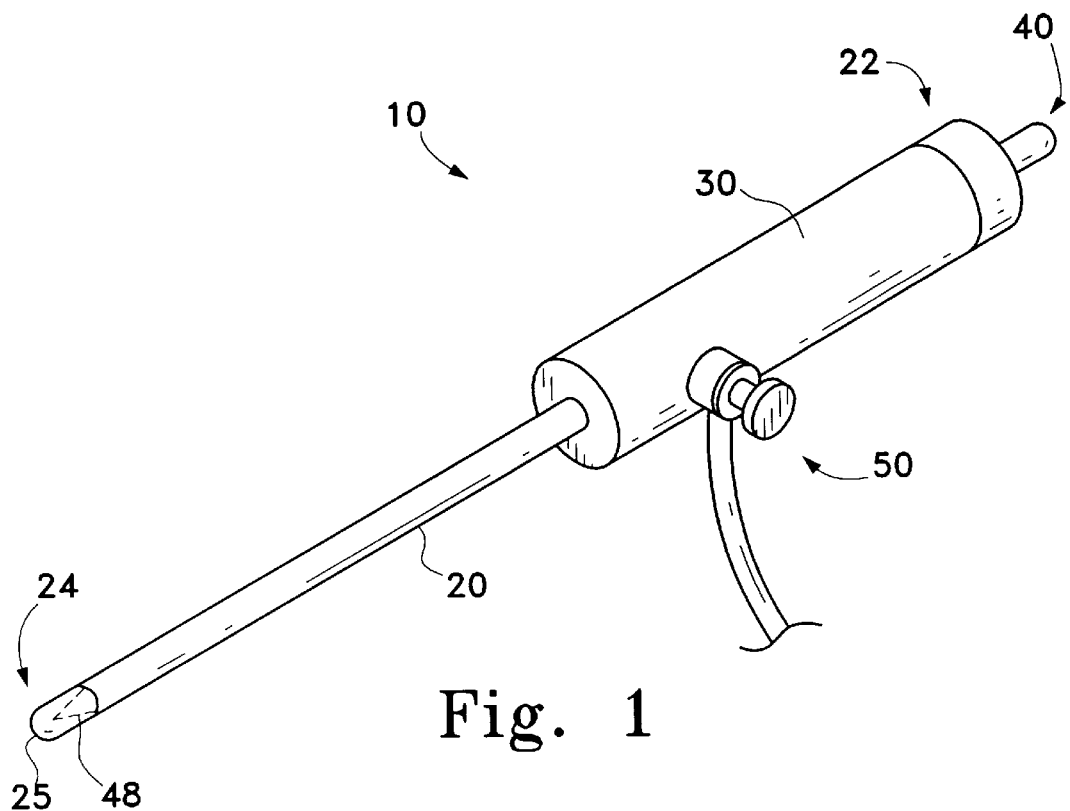
FIG. 1 is a perspective view of a surgical cutting instrument constructed in accordance with the principles of the present invention.

A first embodiment of the surgical cutting instrument 10 of the present invention is illustrated in FIG. 1. Surgical cutting instrument 10 includes an outer shaft 20 having a proximal end 22, an open distal end 24, and an axial lumen 26 between the proximal and distal ends of the shaft 20 (see FIG. 2A). Preferably, the distal end 24 of the shaft 20 includes a rounded or blunt cap 25 made from a clear plastic material to minimize trauma during the introduction of the cutting instrument 10 into the body cavity and to allow for visual confirmation of the position of the cutting element 48 within shaft 20. Shaft 20 is integrally connected within an axial bore 29 to a handle 30 at the proximal end 22 of the shaft 20. Handle 30 is configured to be grasped by the surgeon to allow the surgeon to grip and support the surgical cutting instrument 10 during surgery. Shaft 20 is preferably a rigid, metal or plastic tube having an outer diameter of between about 3 and 10 mm, and preferably between about 3 to 5 mm, so as to fit within a trocar sleeve percutaneously positioned in a patient's chest wall, as will be explained in greater detail below. Shaft 20 can also be introduced directly through a percutaneous incision in the chest. Shaft 20 must have a sufficient length to reach a target site within a body cavity, such as the heart, from a position outside of the body. Typically, shaft 20 will have a length of between about 10 and 30 cm. Shaft 20 is shown in the drawings as having a generally circular cross-sectional configuration. However, it is within the scope of the invention for shaft 20 to have other configurations, including, but not limited to, square, rectangular, oval, or channel or any other cross-sectional configuration. Additionally, shaft 20 could be curved or angled.

Figure 2A:
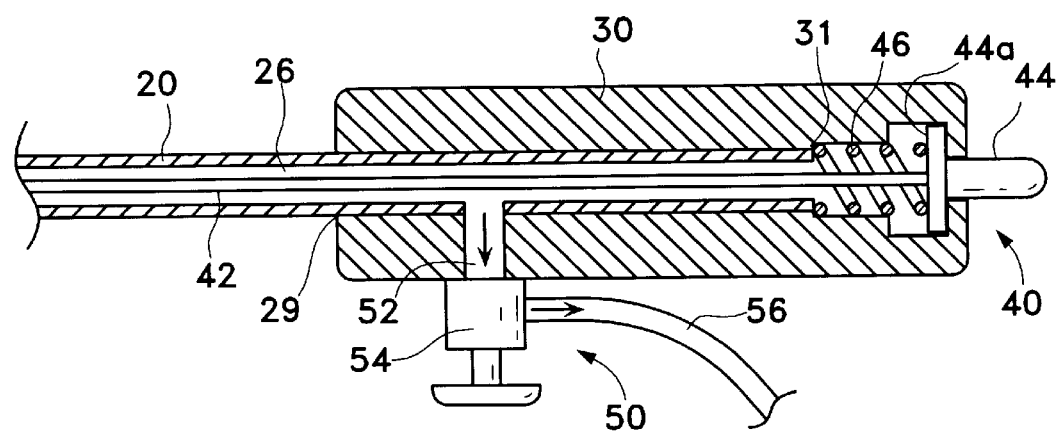
FIG. 2A is a sectional view of the proximal portion of the surgical cutting instrument of FIG. 1.
Figure 3A:
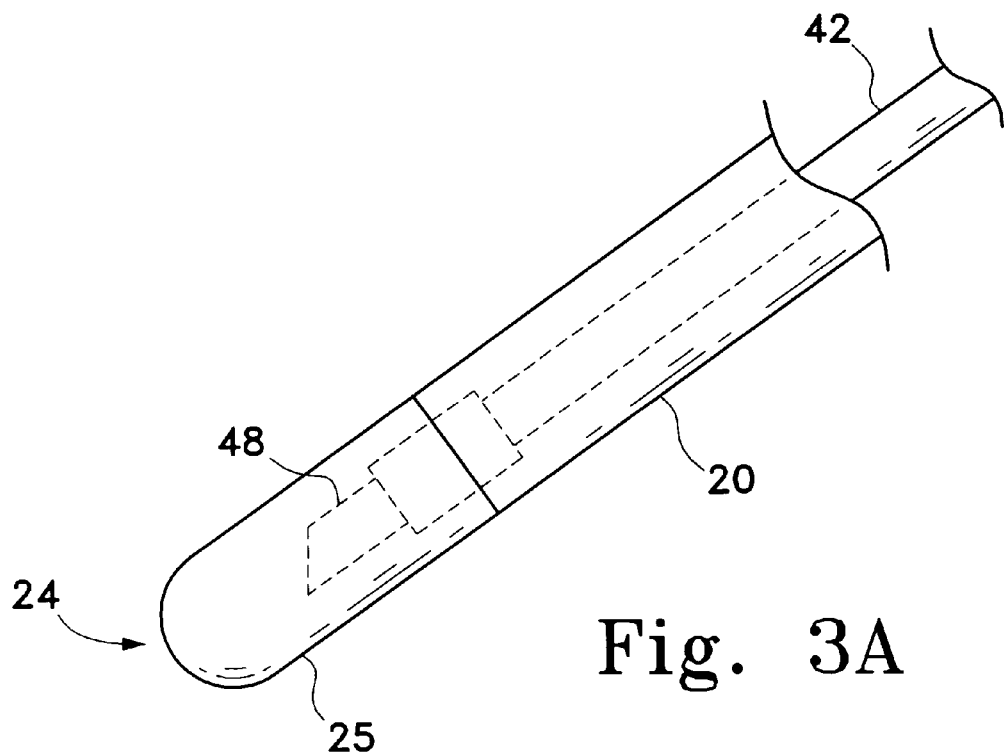
FIG. 3A is a schematic view of the distal portion of the surgical cutting instrument of FIG. 1 showing the cutting element in a retracted position within the shaft of the instrument.
Figure 3B:
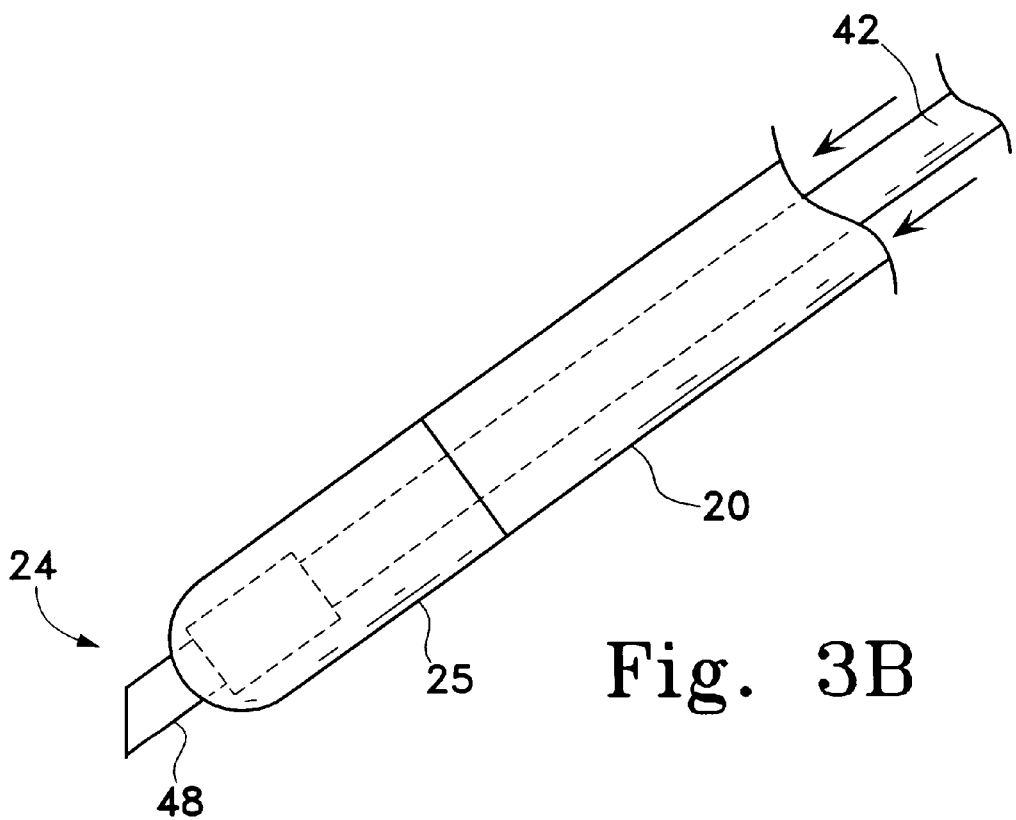
FIG. 3B is a schematic view of the distal portion of the surgical cutting instrument of FIG. 1 showing the cutting element extending a short distance beyond the distal end of the shaft in a cutting position.

Referring now to FIG. 2A, a push-button actuated inner cutting assembly 40 is shown which is movably disposed within shaft 20. Cutting assembly 40 includes a cutting element 48 in the form of a sharpened blade located within shaft 20 at the distal end of the shaft 20. As shown in FIG. 3A, blade 48 is shielded by rounded cap 25 in the retracted position of the blade 48 to prevent injury to surrounding tissues and internal body structures during insertion of the instrument 10 into a body cavity. Blade 48 is fixed to an actuator button 44 by a push rod 42. A spring 46 is located within handle 30 between inner support 31 and an inner surface 44a of button 44, to bias the actuator button 44 into the retracted, closed configuration of FIG. 3A in which cutting element 48 is covered by the distal end of shaft 20. Actuation of button 44 by the surgeon will cause blade 48 to move axially within shaft 20 to protrude a slight distance beyond the cap 25 of the shaft 20 for cutting a body structure, as shown in FIG. 3B and as will be explained in greater detail below.

A vacuum control assembly 50 is mounted to the handle 30 by threading, welding, brazing or other equivalent mounting method, for creating a suction holding force at the distal end of the shaft 20. The handle 30 is provided with an internal vacuum lumen 52 which connects the vacuum control device 54 to the shaft lumen 26. The vacuum control device 54 is preferably a vacuum "on/off" mechanism, but may be any other equivalent mechanism that operates to selectively open and close the vacuum pathway provided by internal vacuum lumen 52. A CLIPPARD MINIMATIC® three way poppet valve, Model No. MAV-3, Cincinnati, Ohio, is a preferred vacuum control device for use in the vacuum control assembly, and threadably engages with the handle 30. A vacuum hose 56 connects the vacuum control device 54 with an external vacuum source (not shown).

Vacuum applied from the vacuum source is then effectively applied at the distal end of the lumen 26 via the pathway provided by components 56, 54, 52 and 26. In the embodiment shown in FIG. 2, the application of vacuum to the distal end of the lumen 26 is initiated by pressing "on/off" button 51 of the vacuum control device 54, and discontinued by releasing the button. Thus, the vacuum "on/off" button 51 is operable to connect the vacuum conduit 52 to the vacuum source to create a suction force within shaft lumen 26 when the button 51 is actuated by the user, as will be explained in greater detail below. The suction force created within lumen 26 by actuation of vacuum "on/off" button 51 is sufficient to retain a surface of the body structure, such as a blood vessel, adjacent (e.g., in contact with or near) the distal, open end 25 of shaft 20 to facilitate the cutting procedure.

Although one configuration of a vacuum control assembly has been disclosed, it is to be understood that other configurations are within the scope of the present invention. For example, a vacuum control valve, such as a "trumpet"-type valve or slide valve, described below in connection with the embodiment of FIGS. 11–13, or other similar valve mechanism, could be coupled to or incorporated into handle 30 to control the pressure within shaft 20 of surgical cutting instrument 10.

Figure 2B:
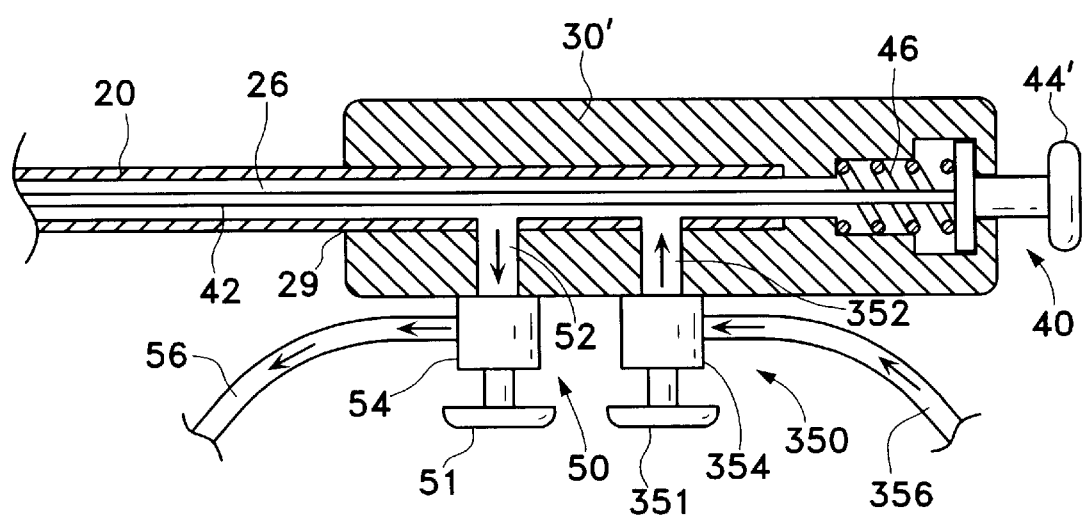
FIG. 2B is a sectional view of the proximal portion of a variation of the surgical cutting instrument of FIG. 2A, further including an irrigation feature.

The surgical cutting instrument 10 may further include an irrigation control assembly 350 mounted to the handle 30', by threading, welding, brazing or other equivalent mounting method, as shown in FIG. 2B, for providing an irrigation fluid at the distal end of the shaft 20. The handle 30' is provided with an internal irrigation lumen 352 which connects the irrigation control device 354 to the shaft lumen 26. The irrigation control device 354 is preferably an "on/off" mechanism, but may be any other equivalent mechanism that operates to selectively open and close the irrigation fluid pathway provided by internal irrigation lumen 352. A CLIPPARD MINIMATIC® three way poppet valve, Model No. MAV-3, Cincinnati, Ohio, is a preferred irrigation control device for use in the irrigation control assembly, and threadably engages with the handle 30'. An irrigation hose 356 connects the irrigation control device 354 with an external source that provides irrigation fluid under pressure (not shown).

Irrigation fluid applied from the external source is then effectively applied at the distal end of the lumen 26 via the pathway provided by components 356, 354, 352 and 26. In the embodiment shown in FIG. 2B, the application of irrigation fluid to the distal end of the lumen 26 is initiated by pressing "on/off" button 351 of the irrigation control device 354, and discontinued by releasing the button. Thus, the irrigation "on/off" button 351 is operable to connect the irrigation conduit 352 to the external source to create a pressurized flow of irrigation fluid within shaft lumen 26 when the button 351 is actuated by the user. The irrigation fluid can be used to clear debris away from the body structure to keep the operative field clear during use of the device.

Although one configuration of an irrigation control assembly has been disclosed, it is to be understood that other configurations are within the scope of the present invention. For example, an irrigation control valve, such as a "trumpet"-type valve or slide valve, or other similar valve mechanism, could be coupled to or incorporated into handle 30' to control the pressure within shaft 20 of surgical cutting instrument 10.

Figure 4A:
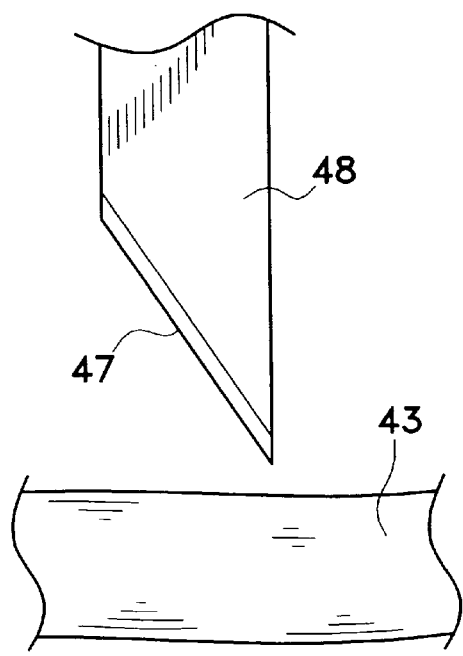
FIGS. 4A–4C are side elevational views of three alternative embodiments of the distal portion of the surgical cutting instrument of FIG. 1.
Figure 4B:
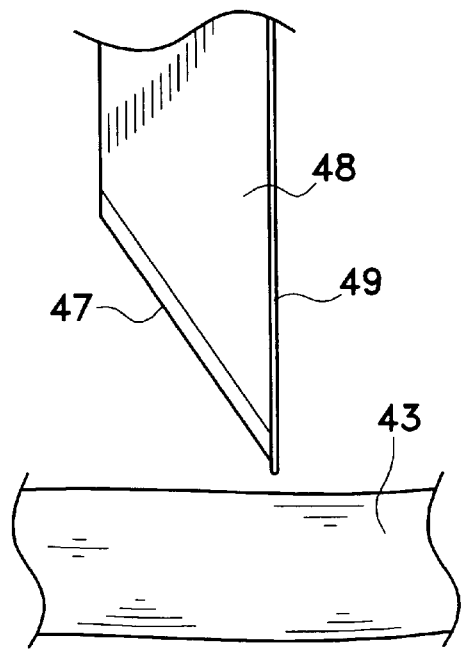
Figure 4C:
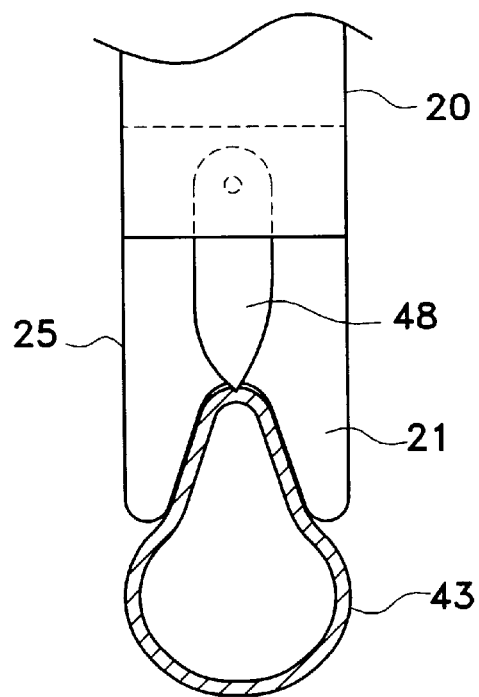

FIGS. 4A–C show various embodiments of the distal end of the cutting assembly 40. As shown in FIG. 4A, blade 48 preferably has a sharpened cutting edge 47 along an inner edge thereof. To optimize the cutting action of cutting edge 47, cutting edge 47 is preferably angled from between about 15 and 30 degrees relative to the vertical axis of the blade. As shown in FIG. 4B, an active electrode 49 electrically connected to an electrosurgical power supply (not shown), such as an RF energy power supply, can be soldered, glued or otherwise affixed alongside the back edge of blade 48. Active electrode 49 will facilitate making an incision in a body structure by making a small point incision, i.e., a pilot hole, in the body structure when activated by the energy supply. In such a configuration, a return, ground electrode in the form of a dispersive electrode pad (not shown) can be connected to an external surface of the patient's body to provide an electrically conductive path from the active electrode to the return electrode, as would be conventional in the art of electrocautery. The pilot hole made by the energized active electrode 49 can then be expanded by the shearing action of cutting blade 48 to make a precise cut in the desired body structure, such as a blood vessel 43. As illustrated in FIG. 4C, the distal end of shaft 20 may have various configurations to facilitate the cutting action of blade 48. For example, as shown in FIG. 4C, the cap 25 at the distal end of shaft 20 can have a notched head configuration 21 which is configured to pinch or squeeze the body structure into shaft 20 adjacent blade 48. The squeezing action of notched head 21 brings the desired tissue segment into close proximity to blade 48, which can then be plunged into the pinched tissue segment to facilitate the cutting operation.

Although a few various configurations of the cutting element 48 and the distal end 24 of shaft 20 have been disclosed in the drawings, it is to be understood that the invention is not limited to the foregoing configurations. For example, the shaft 20 could be provided with an integral gripping element, such as, for example, that described below with regard to the embodiment shown in FIGS. 16–19. In addition, cutting element 48 can have various configurations. For example, the cutting element can be in the form of an ultrasonic scalpel 448, as shown in FIG. 14A.

The ultrasonic scalpel 448 is energized by a tool tip ultrasonic transducer 450 which is electrically connected to an ultrasonic generator 452 (shown schematically in FIG. 15) that is external of the tool. The ultrasonic transducer 450 vibrates (preferably longitudinally) to transmit the vibration to the ultrasonic scalpel 448 at a controlled ultrasonic frequency. The ultrasonic transducer 450 may include a piezoelectric crystal or a magneto-restrictive transducer that is capable of being electromagnetically excited. The ultrasonic transducer 450 is electrically connected to the ultrasonic generator 452 through the shaft 20 and handle 430. An electrical line 434 leads from handle 430 to connect with the ultrasonic generator 452 (not shown in FIG. 14B). The ultrasonic generator contains a switch (not shown) that allows the operator to "on/off" control the application of ultrasonic vibrations to the ultrasonic scalpel 448. Such a configuration could allow division of tissues with low heat, producing minimal vaporized tissue compared with the electrocautery approach of FIG. 4B.

Although an actuator in the form of a sliding push button (44, 44') has been described in representative embodiments, various types of actuator mechanisms may be used to slide cutting element 48 with respect to shaft 20 and handle 30, including, for example, a plunger mechanism, a rotatable knob that converts rotational motion into axial motion, or a motor-driven linear actuator mechanism.

Figure 5:
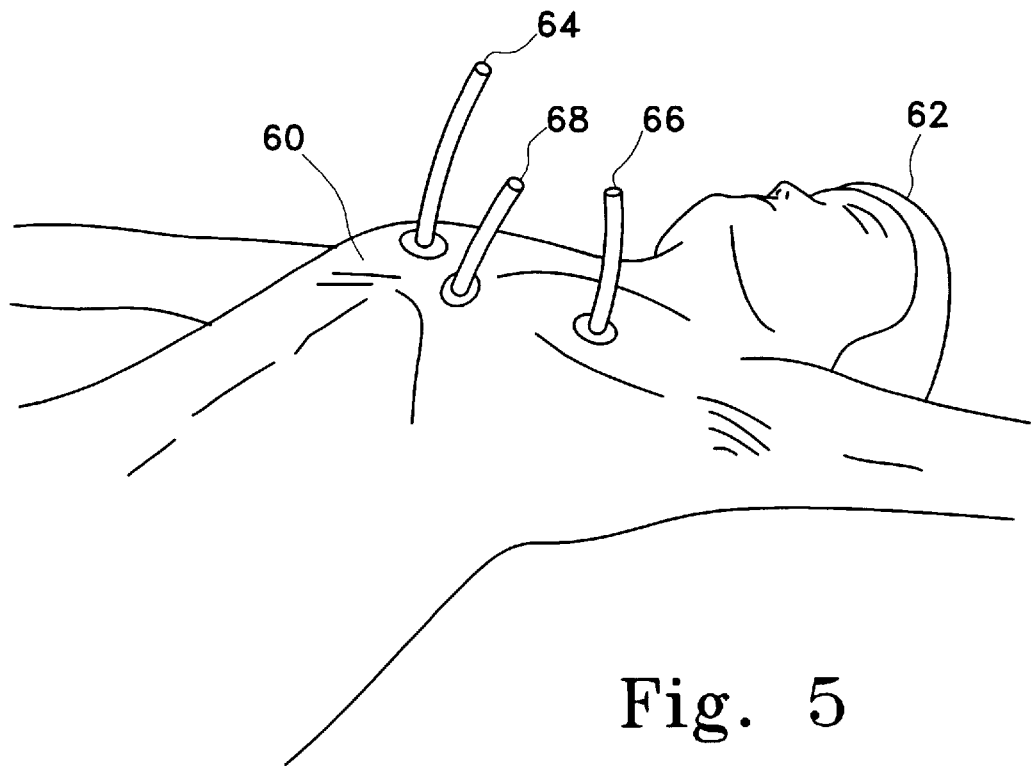
FIG. 5 is a perspective view of a patient during minimally invasive surgery.
Figure 6:
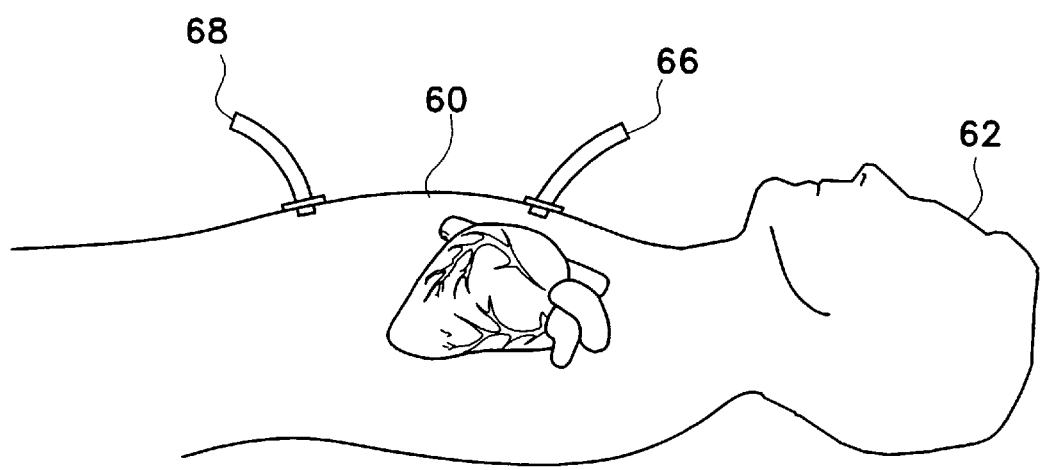
FIG. 6 is a side view of the patient of FIG. 5 prior to insertion of the surgical cutting instrument into the patient's thoracic cavity through one of the percutaneously positioned trocar sleeves.
Figure 7:
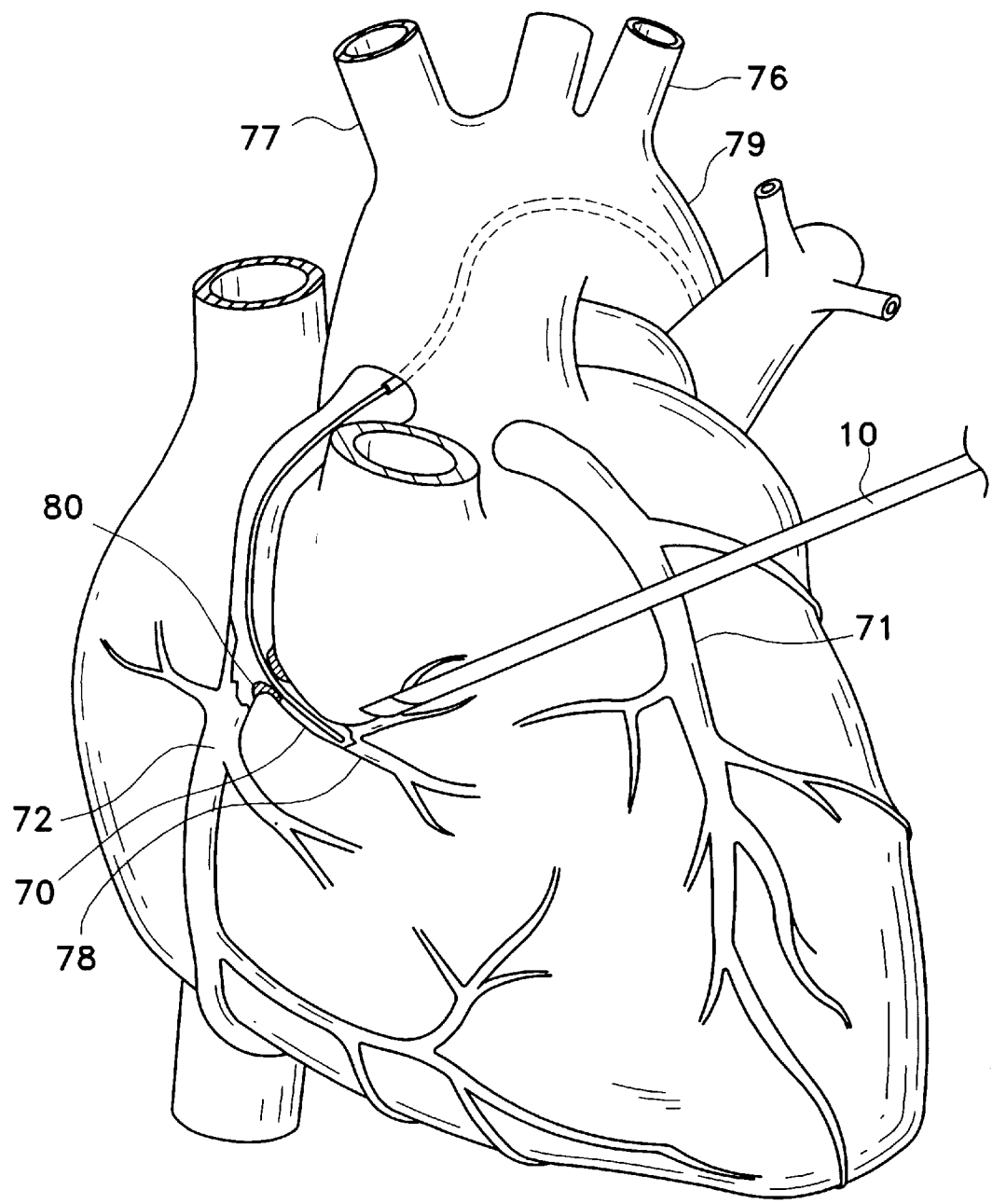
FIG. 7 is an illustration of a patient's heart illustrating the use of the instrument of FIG. 1 inserted through a trocar sleeve, and illustrating a transillumination catheter for identifying the blockage in a coronary vessel.

FIGS. 5 through 7 illustrate a representative thoracoscopic cutting procedure according to the present invention. While a preferred method of performing a coronary artery anastomosis in a thoracoscopic CABG procedure will be described below, it is to be understood that the principles of the present invention may be applied to a wide variety of surgical procedures, both conventional, open procedures, as well as minimally invasive procedures. After placing a patient under general anesthesia, the patient's left lung is deflated using conventional techniques. Multiple small percutaneous incisions are made in the chest wall for the receipt of surgical instruments. As used herein, the term "percutaneous" refers to any penetration through the skin of the patient, whether in the form of a small cut, incision, hole, cannula, trocar sleeve or the like, which is preferably made in an interstitial space between the ribs of the patient. For example, two small incisions are made in the chest wall 60 of a patient 62 at different interstitial positions between the patient's ribs, while a third incision is made just below the sternum. A first trocar 64 or other access device is inserted into the first incision at one of the interstices and a second trocar 66 is inserted into the second incision. A third trocar 68 is inserted into the third incision just below the sternum.

Each trocar is conventional and includes a central conduit (not shown) for the insertion of surgical instruments, tubes, etc. An example of a trocar which can be used in the present invention is a "THORACOPORT"™5 mm trocar manufactured by United States Surgical Corporation of Norwalk, Conn. Once the trocars are installed, a conventional viewing device such as an endoscope, thoracoscope or other viewing instrument is inserted into one of the trocars for viewing of the operative site within the internal thoracic cavity during the surgical procedure.

The invention will now be described in reference to making an arteriotomy incision in a diseased right coronary artery downstream from a blockage, or stenosis, in the artery during a coronary anastomosis procedure. The heart is schematically represented in FIG. 7. Very generally, the heart includes an aorta 79 which supplies blood to the major organs of the body, left and right subclavian arteries 76 and 77, respectively, which supply blood from the aorta to the arms and other upper portions of the body, a left 71 and right coronary artery 72 which provide blood to the heart itself, as well as marginal branches off of the left and right coronary artery, such as marginal branch 78 shown with a blockage 80. Conventional coronary bypass graft procedures first require that a source of arterial blood be prepared for subsequent bypass connection to the diseased artery. An arterial graft can be used to provide a source of blood flow, or a free graft vessel can be used and connected at the proximal end to a source of blood flow. Preferably, the source of blood flow is any one of a number of existing arteries that are dissected in preparation for the bypass graft procedure. In many instances, it is preferred to use either the left or right internal thoracic artery (not shown). In multiple bypass situations, it may be preferable to use free graft vessels such as the saphenous vein, gastroepiploic artery in the abdomen, and other arteries harvested from the patient's body. If a free graft vessel is used, the upstream end (proximal) of the dissected vessel is connected to the aorta 79 to provide the desired bypass blood flow, and the downstream end (distal) of the dissected vessel will be connected to the diseased target vessel in a distal anastomosis.

The target bypass graft vessel can be dissected and prepared for coronary anastomosis using a conventional electrosurgical instrument (not shown) and a viewing scope introduced through any one of the trocars in the chest wall 60 of the patient 62 (FIGS. 5 & 6). A transillumination catheter 70 (see FIG. 7) and method such as fully described in co-pending application Ser. No. 09/042,433 filed on Mar. 13, 1998, for "Transillumination Catheter and Method" and invented by Francis G. Duhaylongsod, M.D. and Hugh Narciso, Jr., which is fully incorporated by reference herein, can be used to facilitate the process of locating and manipulating the target bypass graft vessel to identify the vessel prior to dissecting it.

After the bypass graft vessel has been prepared for coronary anastomosis, the heart can be arrested and intermittently electrically paced using the novel TRANSARREST™ system which is fully described in co-pending provisional patent application Ser. No. 60/055,127, for "Compositions, Apparatus, and Methods For Facilitating Surgical Procedures," filed on Aug. 8, 1997, and invented by Francis G. Duhaylongsod, M.D., the entire contents of which are fully incorporated by reference herein.

Subsequently, an arteriotomy incision is required in the diseased vessel downstream from a blockage in the vessel to facilitate the anastomosis procedure. As shown in FIG. 7, to facilitate locating the blockage 80 in one of the marginal branches 78 of the right coronary artery 72 downstream from which an arteriotomy incision is needed, the transillumination catheter 70 described above and in co-pending patent application Ser. No. 09/042,433 can be used. The transillumination catheter 70 is percutaneously inserted into a peripheral vessel, such as a brachial artery or a femoral artery (not shown), and advanced with the aid of x-ray fluoroscopy or other guidance means, such as transesophageal echocardiography, into the diseased right coronary artery 72 and/or its marginal branch 78 to provide illumination of the artery. Alternatively, the transillumination catheter 70 can be placed directly in the right coronary artery 72 by a surgical technique using surgical cutting instrument 10 introduced through a trocar sleeve to make an insertion incision in the vessel. Once the catheter 70 is properly positioned in the stenosed marginal branch 78 of right coronary artery 72, the lateral diffusion of light from the distal end of the catheter will help the surgeon to identify the location of the blockage 80. The thicker wall associated with the diseased, calcified portion of the vessel will diminish the amount of light that passes through the vessel to help the surgeon locate where in the vessel to make the arteriotomy incision.

Once the proper location for making the arteriotomy incision is found, the surgical cutting instrument 10 is used to make an incision in the artery downstream from the stenosed region. Preferably, the surgical cutting instrument 10 is introduced into the thoracic cavity through one of the trocar sleeves of FIGS. 5 and 6. Alternatively, the surgical cutting instrument 10 can be inserted directly through a percutaneous incision in the chest wall without using a trocar sleeve or other similar introducer device. The use of a trocar sleeve, however, is preferred to provide an open passage into the thoracic cavity and to prevent injury to adjacent tissues and the like during insertion of the instrument. With the surgical cutting instrument 10 positioned adjacent the external surface of a vessel as shown in FIG. 7, the surgeon can push the vacuum "on/off" button 51 to create a vacuum within shaft lumen 26. The resultant suction force created at the open, distal end 24 of the shaft 20 will cause the vessel to be held or retained adjacent (in contact with or near) the distal end of the shaft.

With the vessel so held by the surgical cutting instrument 10, the surgeon can then press on the actuator push button 44 to cause cutting element 48 to move axially within shaft lumen 26 along the longitudinal dimension of the shaft. This will cause blade 48 to protrude a short distance beyond the distal end of the shaft 20 as shown in FIG. 3B. Blade 48 will make contact with the wall of the target vessel and thereby make a fine cut in the wall of the vessel. After a cut has been made in the vessel, the surgeon can then release the vacuum "on/off" button 51 to turn off the vacuum and release the vessel from engagement with the surgical cutting instrument 10. Subsequent release of the actuator push button 44 by the surgeon will cause the cutting element 48 to be retracted back into the shaft 20. This procedure can be repeated one or more times to make an incision of a desired depth and length in the diseased vessel. It is to be understood that the one or more incisions in the vessel can be made with the heart arrested or beating. In the latter case, the suction force created at the distal end of the shaft helps to compensate for and minimize the movement of the target area to be incised.

After the arteriotomy incision is made in the diseased vessel, the bypass graft vessel can be anastomosed to it at the site of the arteriotomy incision using conventional suturing techniques and microsurgical working instruments introduced through the trocar sleeves. Alternatively, the coronary anastomosis procedure can be performed using any one of the novel anastomosis devices and methods described in co.-pending patent application Ser. Nos. 09/037,109; 09/037,113 and 09/037,216 for "Anastomosis Device and Method", each filed on Mar. 9, 1998, the entire contents of which are incorporated by reference herein.

Figure 8:
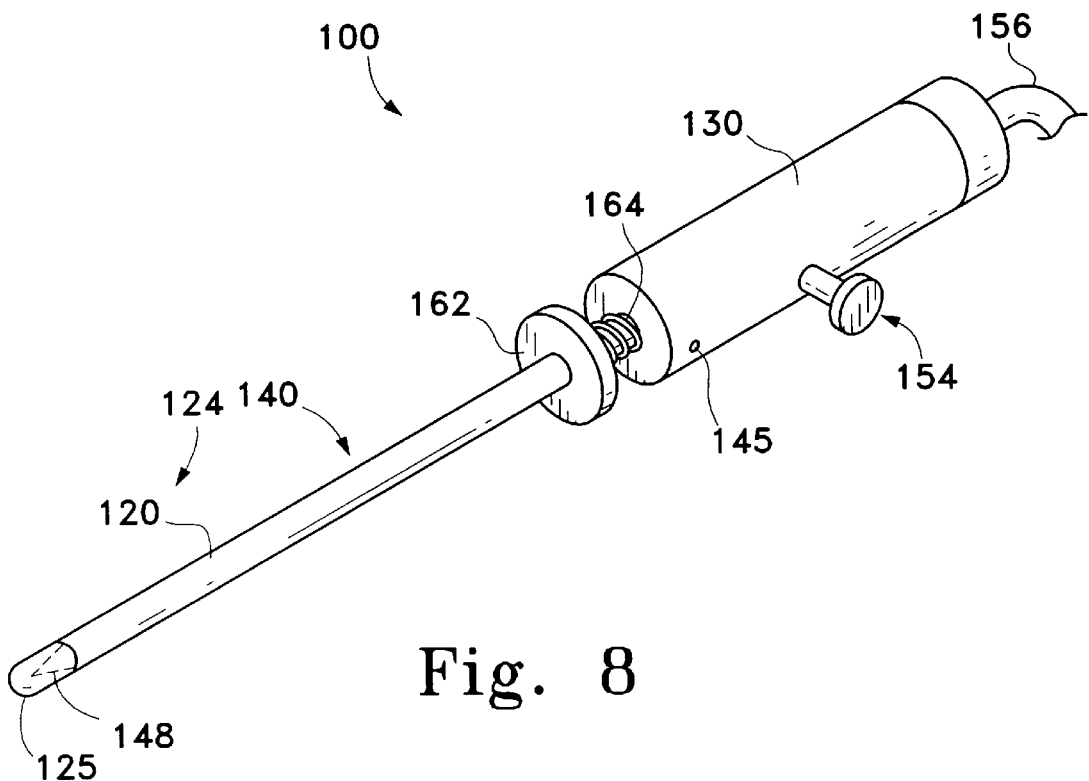
FIG. 8 is a perspective view of another embodiment of a surgical cutting instrument.
Figure 9:
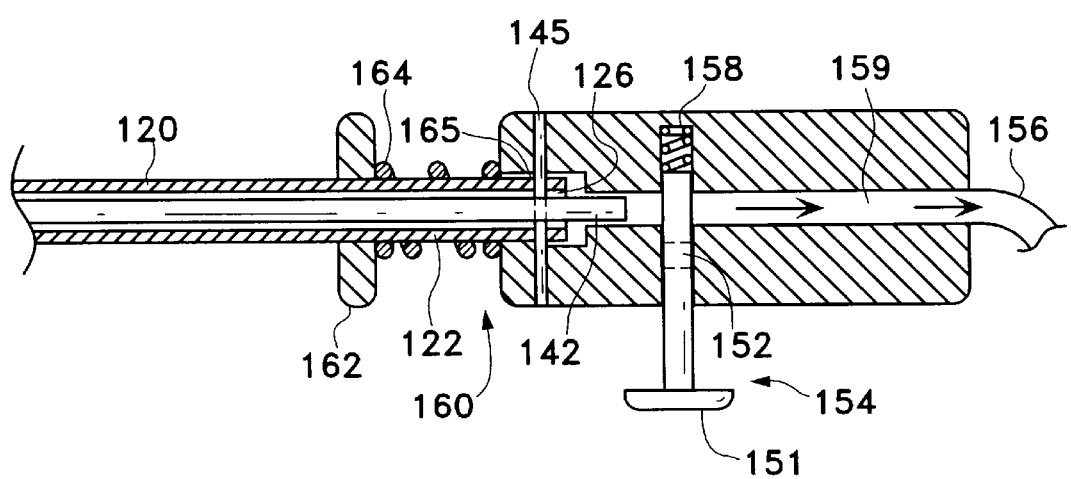
FIG. 9 is a side cross-sectional view of the proximal portion of the surgical cutting instrument of FIG. 8.
Figure 10:
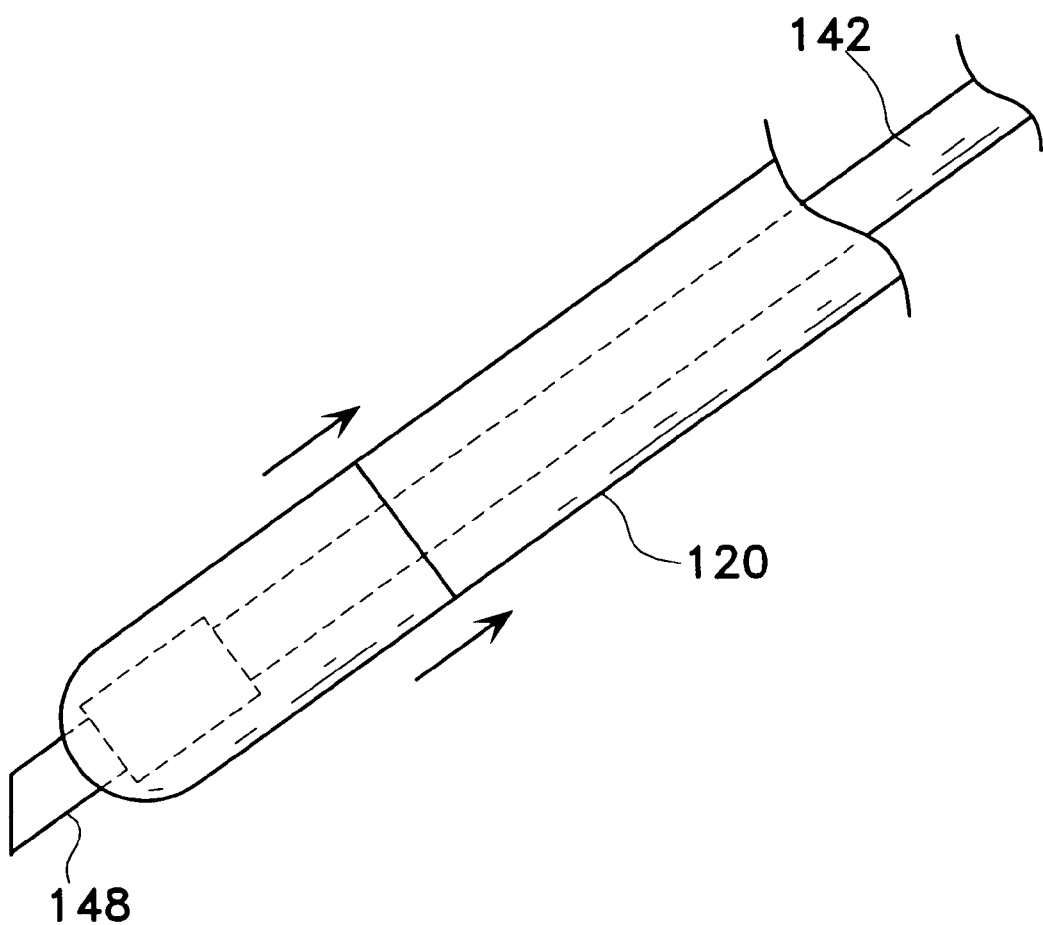
FIG. 10 is a schematic view of the distal portion of the surgical cutting instrument of FIG. 8 showing the cutting element extending a short distance beyond the distal end of the shaft after the shaft has been moved axially over the cutting element.

FIGS. 8–10 illustrate another embodiment of a surgical cutting instrument 100 constructed in accordance with the principles of the present invention. The distal, cutting end portion 124 of instrument 100 has generally the same structure as end structure 24 of instrument 10, with the main difference being that the cutting element 148 is stationary in this embodiment, with the shaft 120 being configured to move in relation to cutting element 148 upon actuation of the device. With regard to the cutting assembly actuating mechanism located at the proximal portion 122 (FIG. 9), the cutting assembly 140 in this embodiment is fixed to handle 130. Specifically, the cutting element, or blade, 148 is fixed to a rigid rod 142 at a distal end of the rod. The rod 142 is rigidly connected to handle 130 at a proximal end of the rod via locking pin 145.

An actuating assembly 160 is connected to shaft 120 to position cutting element 148 in contact with a body structure to be cut. Actuating assembly 160 includes an annular actuator body 162 which is secured about shaft 120 near the proximal portion 122 of the shaft 120. A spring 164 biases the actuator body 162 into a closed, retracted position of the device in which cutting element 148 is shielded by the distal end of shaft 120, as shown in FIG. 8. A pair of slots 165 are provided within the proximal end of the shaft 120 to enable the shaft to move back and forth within handle 130 and over rod 142. Locking pin 145 is inserted through slots 165 to movably secure the shaft 120 to handle 130.

A vacuum control assembly 150 is provided in the handle 130 to controllably connect the lumen of shaft 120 with an external vacuum source, for creating a suction holding force at the distal end of the shaft 120. The handle 130 is provided with an internal vacuum lumen 159 which is connected to a vacuum source (not shown) at the proximal end of the handle via a vacuum hose 156, and which is fluidly coupled to shaft lumen 126 at its other end. To fluidly couple the vacuum source to shaft lumen 126, a spring-biased vacuum "on/off" button 151, which is preferably a slide valve or equivalent "on/off mechanism, is located in handle 130 and interposed between the vacuum lumen 159 and shaft lumen 126. A spring 158 biases vacuum "on/off" button 151 into a closed, "off" configuration, as shown in FIG. 9, for example.

When button 151 is actuated by the surgeon, a channel 152 formed in the on/off mechanism 154 is brought into alignment with vacuum lumen 159 to fluidly connect the vacuum source to shaft lumen 126. The resultant suction force created within lumen 126 at the distal end of the shaft 120 is sufficient to retain a surface of the body structure, such as a blood vessel, adjacent to (e.g., in contact with or near) the distal, open end 125 of shaft 120 to facilitate the cutting procedure. Additionally, the surgical cutting instrument 100 can further include an irrigation port similar to that shown in FIG. 2B fluidly coupled to the shaft lumen 126 near the proximal end of the shaft 120. Alternatively, a valving mechanism similar to on/off mechanism 154 may be employed for control of irrigation fluids through the irrigation port. The irrigation port can be configured to be connected to a source of irrigation fluid for clearing debris away from the body structure to keep the operative field clear during use of the device.

In operation of the device 100, with the surface of a body structure retained by the distal end of shaft 120 using vacuum control assembly 150, a user can then manipulate actuating assembly 160 to position the cutting element 148 in cutting contact with a body structure, as shown schematically in FIG. 10. Specifically, to expose the cutting element 148 beyond the open, distal end of shaft 120, a user, while holding handle 130, can place his or her fingers about annular button 162 and pull the button towards the handle 130 and against the action of spring 164. This will cause the shaft 120 to move axially over rod 142 to expose the cutting element 148 a short distance beyond the distal end of the shaft. The device can now be used for a surgical cutting procedure similar to the embodiment of FIGS. 1–3, for example, to make a precise incision in a coronary vessel to facilitate a thoracoscopic anastomosis procedure or other cardiac surgical procedure.

Figure 11:
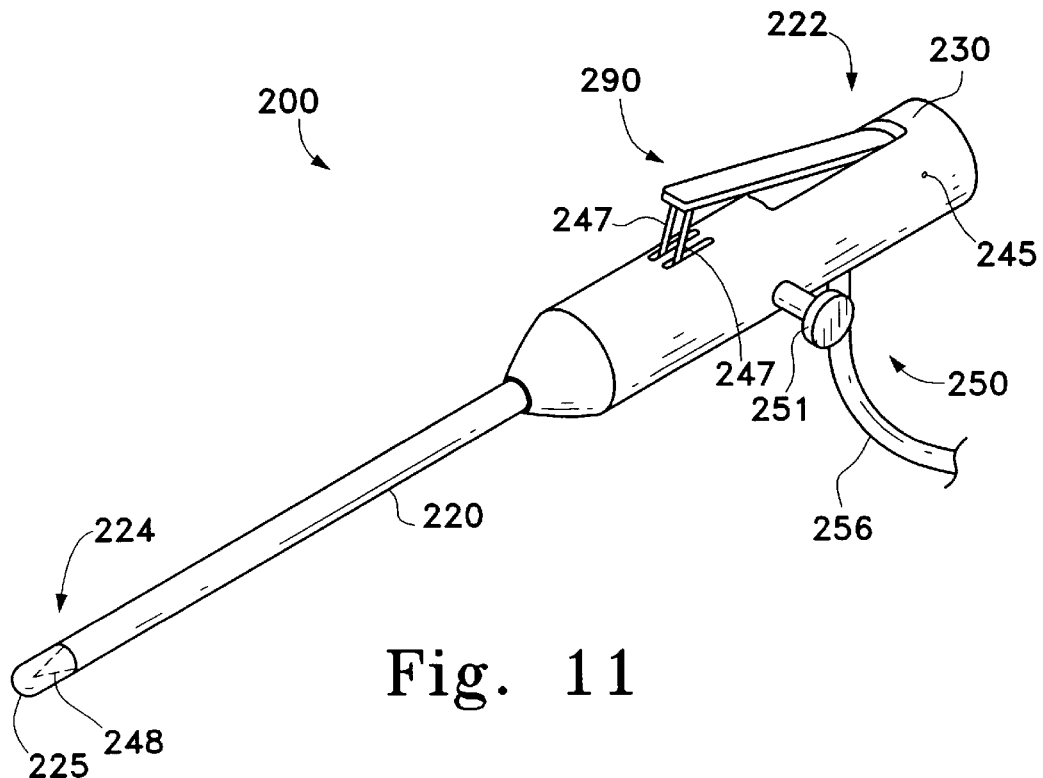
FIG. 11 is a perspective view of a further embodiment of a surgical cutting instrument.
Figure 12:
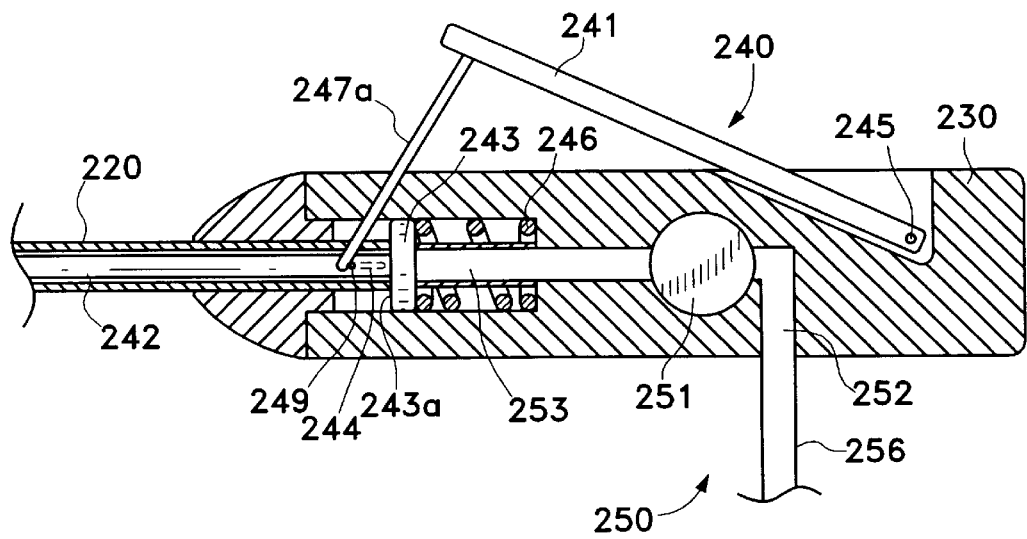
FIG. 12 is a side cross-sectional view of the proximal portion of the surgical cutting instrument of FIG. 11.
Figure 13:
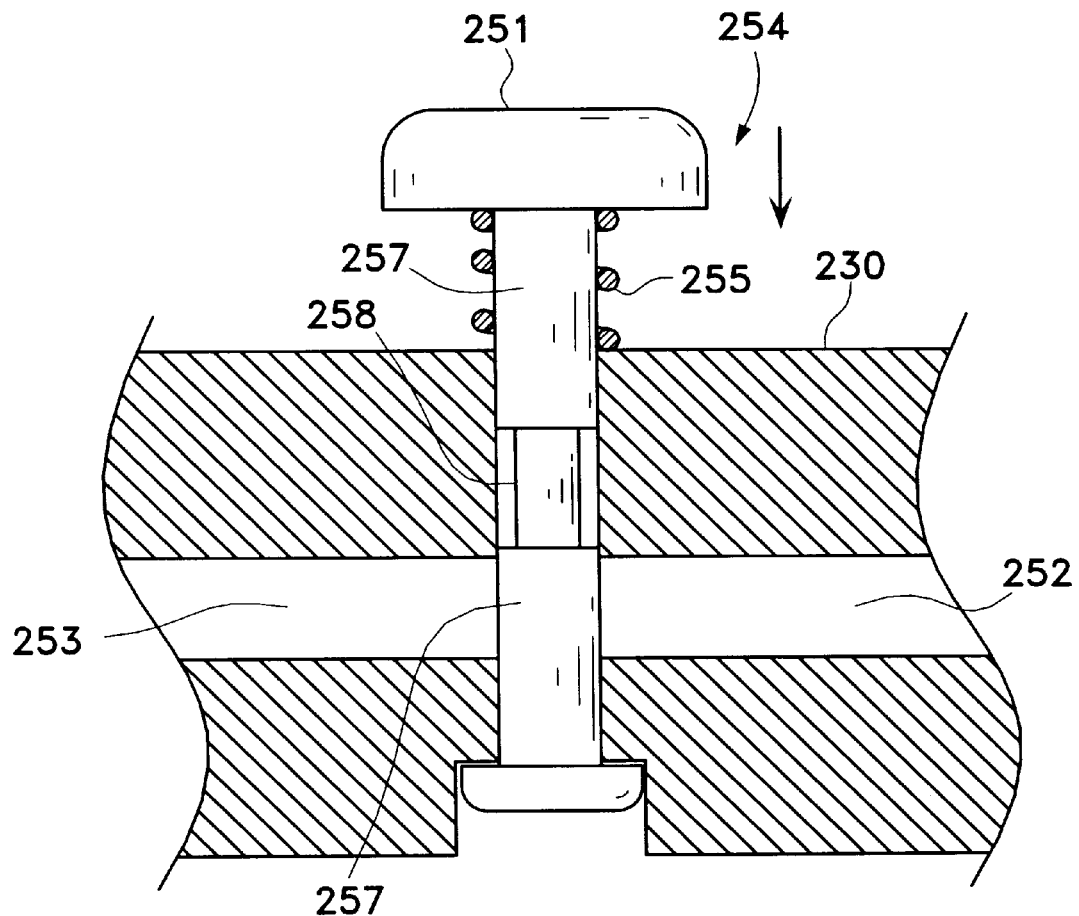
FIG. 13 is a side cross-sectional view of the vacuum control assembly of the surgical cutting instrument of FIG. 11.
Figure 16:
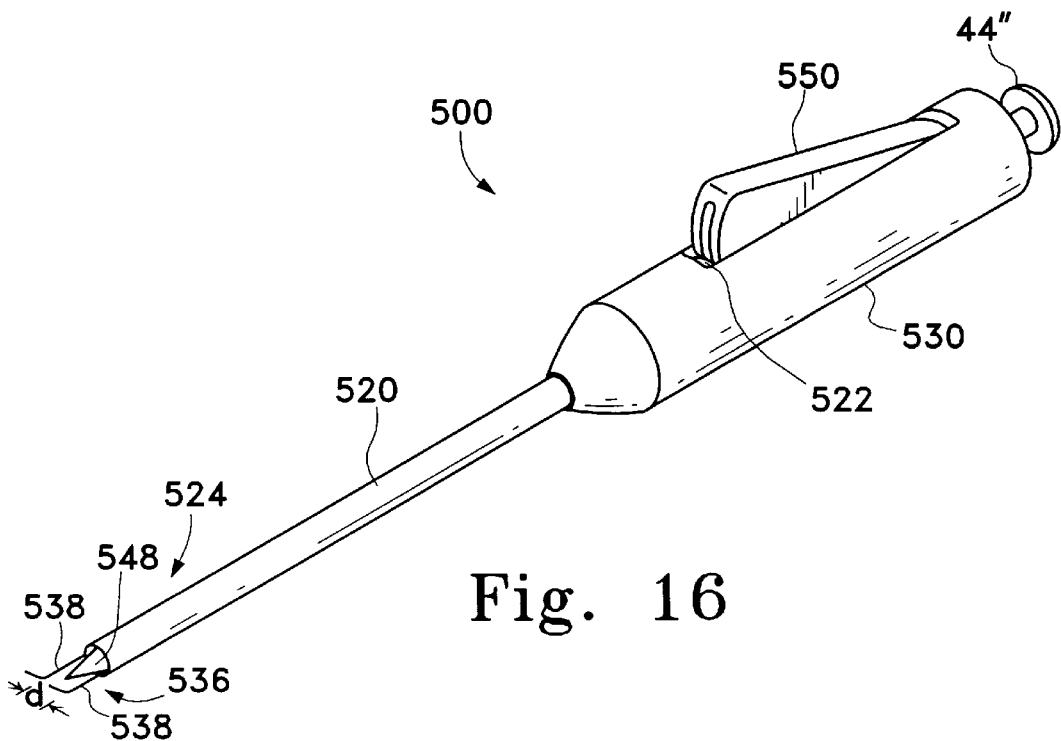
FIG. 16 is a perspective view of an embodiment of the present invention which employs a gripper.

FIGS. 11–13 illustrate another embodiment of a surgical cutting instrument 200 constructed in accordance with the principles of the present invention. Again, the distal, cutting end portion 224 of instrument 200 has generally the same structure as the distal cutting end portion 24 of the surgical instrument 10, with the main difference being that the cutting element 248 is stationary in this embodiment, with the shaft 220 being configured to move in relation to cutting element 248 upon actuation of the device. The cutting assembly actuating mechanism located at the proximal portion 222 of the instrument 200, however, is different. Similar to surgical cutting instrument 100, surgical cutting instrument 200 includes a main shaft 220. Shaft 220 is connected to a clear cap member 225 at the distal end of the shaft which is sized to shield blade 248 upon insertion of the device into a body cavity, and is connected to a spring-biased annular end member 243 at the proximal end of the shaft 220. Shaft 220 is slidably coupled to handle 230 and is configured to move in a longitudinal path relative to handle 230 upon actuation by actuator assembly 240, as is described below in connection with FIG. 12.

As shown in FIG. 12, actuator assembly 240 includes an actuator lever arm 241 which is rotatably connected to handle 230 at the proximal end of actuator arm 241 via a push pin 245 provided in the proximal portion of handle 230. A pair of actuating rods 247 are fixedly connected to lever arm 241 at the distal end of arm 241 and are located on either side of the proximal position of shaft 220. Rods 247 are configured to engage a push pin 249 which is rigidly connected to shaft 220. Push pin 249 is adapted to slide within a slot 244 located through the proximal portion of rod 242. Rod 242 is connected to cutting element 248 at the distal end of rod 242, and is fixedly press-fitted into handle 230 at the proximal end of the rod 242. In this way, shaft 220 is axially movable with respect to both rod 242 and cutting element 248. For example, as the actuator arm 241 is depressed by a surgeon, actuating rods 247 force push pin 249 to move backwards within slot 244. This will cause the shaft 220 to move axially over rod 242 to expose the cutting element 248 a short distance beyond the distal end of the shaft. The device can now be used for a surgical cutting procedure similar to the embodiment of FIGS. 1–3, for example, to make a precise incision in a coronary vessel to facilitate a thoracoscopic anastomosis procedure or other cardiac surgical procedure. When the lever arm 241 is released by the surgeon, a spring 246 biases the annular end member 243 connected to the proximal end of shaft 220 into a closed, retracted position of the device in which cutting element 248 is shielded by the distal end of shaft 220, as shown in FIG. 11. The device can now safely be removed from the body cavity or positioned at another location within the body cavity to make subsequent incisions.

Alternatively, the actuator assembly 240 can be configured without push pin 249 and slot 244. Instead, the inner surfaces 247a of each of rods 247 act as a camming surface which abuts surface 243a of end member 243. Thus, when a user presses on actuator arm 241, camming surfaces 247a abut surface 243a and force end member 243 along with shaft 220, backward to exposed cutting element 248 at the distal end of shaft 220.

Rod 242 is hollow and defines an inner lumen 253 which is fluidly coupled to a vacuum lumen 252 in handle 230 to allow a suction force to be transmitted to the distal end of shaft 220, as will be explained hereafter. A vacuum control assembly 250 is shown in FIGS. 12 and 13 for retaining a body structure adjacent to the distal end of shaft 220 in operation of instrument 200. Vacuum control assembly 250 is operably coupled to handle 230 and shaft 220 for creating a suction holding force at the distal end of the shaft 220. The handle 230 is provided with an internal vacuum lumen 252 which is connected to a vacuum source (not shown) near the proximal end of the handle 230 via a vacuum hose 256, and which is fluidly coupled to axial lumen 253 in rod 242 at its other end. As best seen in FIG. 13, to fluidly couple the vacuum source to lumen 243, a spring-biased vacuum "on/off" button 251 located in handle 230 is interposed between the vacuum lumen 252 and lumen 253. A spring 255 biases vacuum "on/off" button 251 into a closed, "off" configuration. In the closed, "off" configuration of vacuum button 251 shown in FIG. 13, tubular portion 257 of control device 254 substantially impedes the transmittal of a suction force generated by the vacuum source through lumen 252.

When button 251 is actuated by the user into an open, "on" configuration, however, a smaller diameter portion 258 of vacuum control device 254 is brought into alignment with vacuum lumen 252 to fluidly connect the vacuum source to shaft lumen 253. The smaller diameter portion 258 allows the suction force generated by the vacuum source to be transmitted past portion 258 and into and along lumen 253 in rod 242. The resultant suction force created within lumen 253 is transmitted to the distal end of shaft 220 and is sufficient to retain a surface of the body structure, such as a blood vessel, adjacent to the distal end of shaft 220 to facilitate the cutting procedure. Additionally, the surgical cutting instrument 200 can further include an irrigation port which may be similar in configuration to the vacuum port of the present embodiment or to that of FIG. 2B. Also, any of the previously described valve mechanisms may be used to control the irrigation fluid flow through the irrigation port and ultimately, through the lumen 253 and shaft 220. The irrigation port can be configured to be connected to a source of irrigation fluid for clearing debris away from the body structure to keep the operative field clear during use of the device.

FIGS. 16–19 illustrate another embodiment of a surgical cutting instrument 500 constructed in accordance with the principles of the present invention. The distal, cutting end portion 524 of instrument 500 includes gripper assembly 536. The gripper assembly 536 preferably includes a pair of gripper elements 538 in the form of flanged armor or other gripping element sized for grasping a body structure, such as a blood vessel, although the invention is not to be so limited. That is, a different number of gripper elements may be employed, e.g., three, two pair, etc., without departing from the inventive concept thereof.

Figure 17:
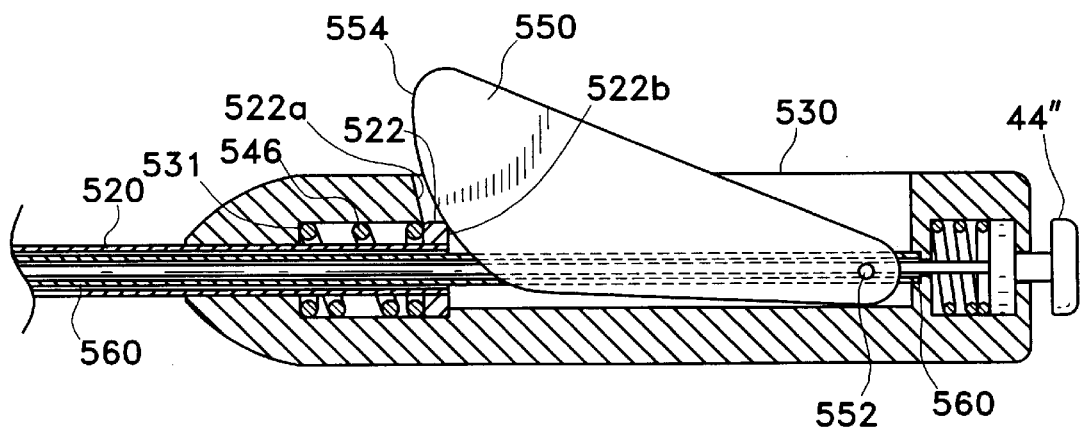
FIG. 17 is a partial sectional view of a proximal portion of the embodiment shown in FIG. 16.
Figure 18:
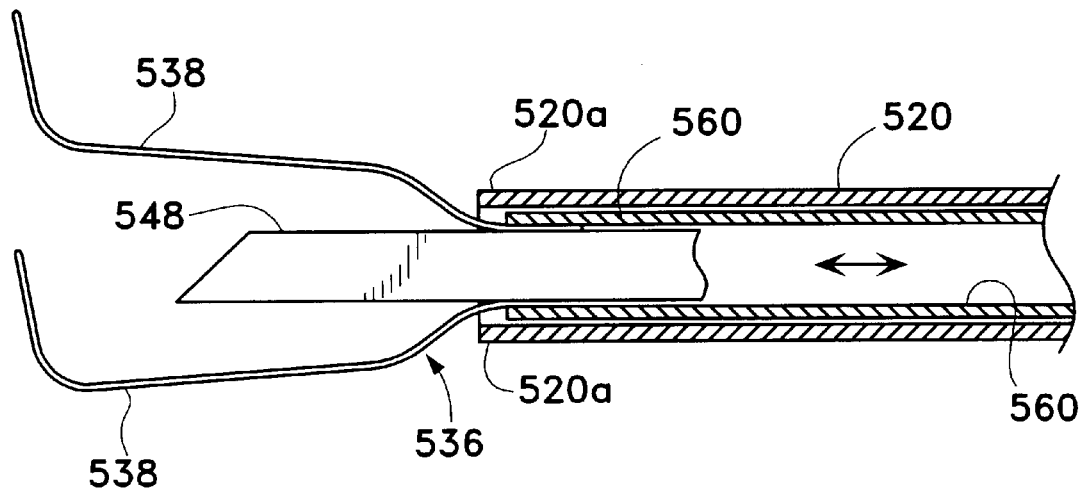
FIG. 18 is a partial sectional view of a distal portion of the embodiment shown in FIG. 16.

The shaft 520 is configured to move in relation to the handle 530 as shown in FIG. 17. A spring 546 is located within handle 530 between inner support 531 and an inner surface 522a of a shoulder 522 that extends from shaft 520, to bias the shaft 520 into the retracted position with respect to the handle 530, as shown in FIG. 17. The gripper elements are spaced by a distance "d" from one another that is greater than the inside diameter of shaft 520 when shaft 520 is in the retracted position shown in FIGS. 16 and 17. The gripper elements are fixed (FIG. 18) to an inner shaft 560 that is immovably mounted with respect to the handle 530 (FIG. 17). A gripper actuator 550 is pivotally mounted to handle 530 by pivot mount 552. The gripper actuator includes a camming surface 554 which abuts surface 522b of shoulder 522 that is opposite surface 522a. The gripper actuator 550 is configured so that an operator can squeeze the gripper actuator 550 and handle 530 together to pivot the gripper actuator 550 toward the handle 530, causing the camming surface 554 to force the shoulder 522 and hence the shaft 520 forward to an extended position with respect to the handle 530.

Figure 19:
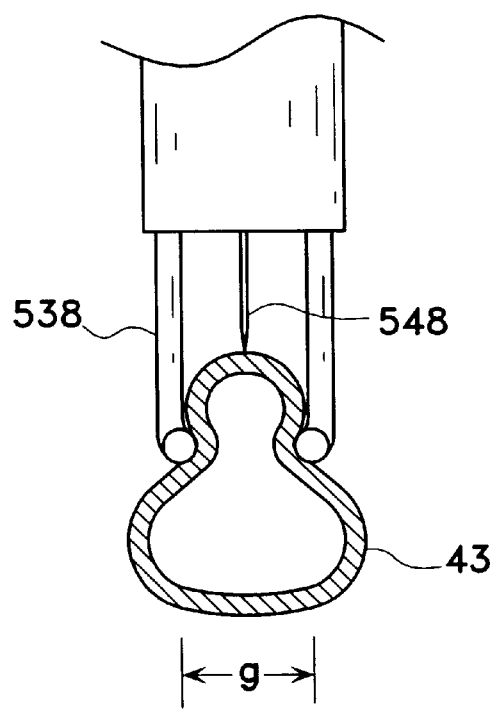
FIG. 19 is a partial sectional view of a vessel as gripped by the grippers of the embodiment partially shown in FIG. 16.

In the meantime, the distal end 520a of the shaft 520 abuts the gripper elements 538 and forces them closer to one another so that they can slide within the inside diameter of the shaft 520, thus causing the gripper elements to assume a "gripping configuration" as shown in FIG. 19. In the "gripping configuration, the gripper elements 538 are separated by a distance "g" which is significantly smaller than the distance "d".

In use, the instrument 500 is inserted into a body cavity with the gripper elements 538 acting to shield the blade 548 from accidental cutting or other damage to body tissues. Once in position, such that gripper members locate on opposite sides of a vessel to be operated upon, the gripper actuator is squeezed by the operator as described above, thereby causing the gripper elements 538 to grip the vessel 43 as shown in FIG. 19. At this time, the vessel 43 is held in a relatively immobile condition with respect to the blade 548, at least in the location of the vessel where the operation is intended to be performed.

The blade 548 is movably mounted with respect to the inner shaft 560 by a mechanism very similar to that described in the first embodiment and shown in FIG. 2B. Although the actuator button 44" is shaped somewhat differently in FIG. 17, it functions the same as buttons 44 and 44' described above. Thus, once the gripper members have been engaged with the tissue to be operated upon as shown in FIG. 19, for example, the operator may then press the actuator button 44" to extend the blade 548 and advance it into the tissue to be cut. When the lever button 44" is released by the operator, the spring 46 biases the blade 548 away from the tissue and into the retracted position shown in FIG. 16. At this time, the instrument 500 can safely be removed from the body cavity or positioned at another location within the body cavity to make subsequent incisions.

Although the gripper assembly 536 is designed to replace the function of the vacuum described above, this embodiment may further include vacuum as described above for purposes of suctioning, etc. Further, the instrument 500 may include irrigation capability using any of the previously described mechanisms for delivering irrigation fluids.

It should be understood that while the above is a complete description of the preferred embodiments of the invention, various alternatives, modifications, and equivalents may be used. For example, the surgical cutting instrument of the present invention can be used to make an incision in any body structure located within the body cavity of a patient, including, but not limited to, a heart, a coronary artery, a coronary vein, an aorta, and any peripheral vessel. The surgical cutting instrument can be adapted to make an incision thoracoscopically or otherwise in any peripheral vessel such as, for example, a saphenous vein, a radial artery, a brachial artery, a gastroepiploic artery, and a subclavian artery, to facilitate a coronary anastomosis procedure and/or the surgical introduction of instruments such as drug delivery catheters, intraluminal shunts, electrical pacing wires, and other similar devices into these and other vessels during surgery.

Therefore, the above description should not be taken as limiting the scope of the invention which is defined by the following claims.

All references cited herein are incorporated by reference.

I claim:

1. A surgical cutting instrument comprising:
   an elongate shaft having a proximal end, a distal end adapted for percutaneous insertion into a body cavity within a patient, and an axial lumen therebetween;
   a stabilizing element associated with said distal end of said shaft; and
   a cutting element disposed within said lumen of said shaft near said distal end;
   wherein said cutting element and said shaft are relatively moveable between a first position and a second cutting position, said cutting element being adapted to cut a body structure within the body cavity when said cutting element and said shaft are in said second cutting position; and
   wherein said stabilizing element, upon actuation, is adapted to grasp an outer surface of the body structure and hold it in a stable position adjacent said distal end.

2. The surgical cutting instrument of claim 1, wherein said instrument is adapted to cut the body structure without removing a substantial portion of the body structure.

3. The surgical cutting instrument of claim 1, wherein said distal end has an outside diameter of less than about 5 mm.

4. The surgical cutting instrument of claim 1, wherein said cutting element comprises at least one blade which has a substantially straight cutting edge.

5. The surgical instrument of claim 4, wherein said cutting edge is displaced at an angle of between about 15 to 30 degrees relative to a vertical axis through the blade.

6. The surgical instrument of claim 5, further comprising an electrode substantially colinearly coupled to said cutting edge.

7. The surgical cutting instrument of claim 1, wherein said cutting element is movably disposed within said lumen of said shaft.

8. The surgical cutting instrument of claim 7, wherein said cutting element comprises at least one blade fixed to a distal end of an actuator push rod located within said lumen of said shaft.

9. The surgical cutting instrument of claim 8, further comprising an actuator button coupled to said actuator push rod at a proximal end of said rod which is operable to move said rod with respect to said shaft to position said cutting element between said first position and said second cutting position.

10. The surgical cutting instrument of claim 9, further comprising a biasing element engaging said actuator button.

11. The surgical cutting instrument of claim 10, wherein said biasing element comprises a spring.

12. The surgical cutting instrument of claim 1, wherein said cutting element comprises at least one blade which is operably coupled to a source of ultrasonic energy.

13. The surgical instrument of claim 1, wherein said stabilizing element comprises a vacuum line fluidly coupled to said lumen of said shaft and adapted to connect to a vacuum to effect a suction force at said distal end.

14. The surgical instrument of claim 13, further comprising a control mechanism positionable to block flow between said vacuum source and said lumen.

15. The surgical instrument of claim 14, wherein said control mechanism comprises a slide valve.

16. The surgical instrument of claim 14, wherein said control mechanism comprises an on/off button.

17. The surgical cutting instrument of claim 1, wherein said body structure is selected from the group consisting of a heart, a coronary artery, a coronary vein, an aorta, and a peripheral vessel.

18. The surgical cutting instrument of claim 17, wherein said peripheral vessel is selected from the group consisting of a saphenous vein, a radial artery, a brachial artery, a gastroepiploic artery, and a subclavian artery.

19. The surgical cutting instrument of claim 1, wherein the body cavity comprises a thoracic cavity.

20. The surgical cutting instrument of claim 1, further comprising at least one electrode disposed near said distal end of said shaft.

21. The surgical cutting instrument of claim 20, further comprising a connector associated with said proximal end of said shaft for electrically coupling said electrode to an electrosurgical power supply.

22. The surgical cutting instrument of claim 1, wherein said stabilizing element comprises a gripper assembly associated with said distal end of said shaft and configured to grip a portion of the body structure.

23. The surgical cutting instrument of claim 1, further comprising a handle connected to said proximal end of said shaft and adapted to be held by at least one hand of a user.

24. The surgical cutting instrument of claim 1, further comprising an irrigation port fluidly coupled to said lumen near said proximal end of said shaft, said irrigation port being connectable to a source of irrigation fluid for clearing debris away from the body structure.

25. The surgical cutting instrument of claim 1, wherein said shaft is movably disposed with respect to said cutting element.

26. The surgical cutting instrument of claim 25, further comprising a handle disposed at said proximal end of said shaft, said shaft being slidably mounted to said handle.

27. The surgical cutting instrument of claim 26, further comprising an anchor fixedly connecting said cutting element to said handle.

28. The surgical cutting instrument of claim 27, wherein said anchor comprises a rod coaxially disposed within said shaft.

29. The surgical cutting instrument of claim 25, further comprising a handle disposed at said proximal end of said shaft, said proximal end of said shaft being slidably mounted within said handle.

30. The surgical cutting instrument of claim 29, further comprising an anchor fixedly connecting said cutting element to said handle.

31. The surgical cutting instrument of claim 30, wherein said anchor comprises a rod coaxially disposed within said shaft.

32. The surgical cutting instrument of claim 25, further comprising an actuator member mounted to said shaft.

33. The surgical cutting instrument of claim 32, wherein said actuator member is mounted near said proximal end of said shaft.

34. The surgical cutting instrument of claim 32, further comprising a biasing element engaging said actuator member.

35. The surgical cutting instrument of claim 34, wherein said biasing element comprises a spring interposed between said actuator member and said handle, wherein said spring biases said shaft to said first position.

36. The surgical instrument of claim 1, further comprising an electrode operatively coupled to said cutting element.

37. The surgical cutting instrument of claim 32, further comprising a lever mounted to said handle and movable to engage said actuator member to move said shaft between said first position and said second cutting position.

38. A surgical cutting instrument adapted for percutaneous insertion into a body cavity within a patient comprising:
an elongate shaft having a proximal end, a distal end, and an axial lumen therebetween;
means for grasping an outer surface of a body structure within said body cavity to hold the body structure adjacent to or near the distal end of the shaft;
a cutting element disposed within said lumen of said shaft near a distal; and
an actuator member disposed near the proximal end of the shaft which is operable to position the cutting element in contact with the body structure for cutting the body structure without substantially removing any portion of the body structure when said grasping means holds the body structure adjacent to or near said distal end of said shaft.

39. The surgical cutting instrument of claim 38 wherein said shaft is moveable between a first position and a second position and is adapted to substantially cover the cutting element when in said first position and to expose at least a portion of the cutting element when in said second position.

40. The surgical cutting instrument of claim 39, wherein said actuator member includes an actuator body fixed to said shaft near said proximal end of said shaft and operable to move said shaft between said first position and said second position.

41. The surgical cutting instrument of claim 40 further including a spring coupled to said actuator body for biasing said shaft into said first position.

42. The surgical cutting instrument of claim 38 wherein said cutting element is moveable between a first position and a second position, said shaft substantially covering said cutting element in said first position, and at least a portion of said cutting element extending from said distal end of said shaft in said second position.

43. The surgical cutting instrument of claim 38, wherein said retaining means comprises a vacuum source fluidly coupled to said lumen of said shaft and operable to produce a suction force at the distal end of the shaft which is sufficient to retain the distal end of the shaft adjacent to or near the surface of the body structure.

44. The surgical cutting instrument of claim 38, wherein said retaining means includes a gripper assembly at said distal end of said shaft which is configured to grip a portion of the body structure to retain the body structure adjacent to said distal end.

45. The surgical cutting instrument of claim 38, further comprising an irrigation port fluidly coupled to said lumen near said proximal end of said shaft.

46. A surgical cutting instrument comprising:

a shaft having a proximal end, an open distal end, and an axial lumen therebetween;

an inlet opening, fluidly coupled to said lumen at said proximal end of said shaft, connectable to a vacuum source for creating a suction force sufficient to retain said distal end of said shaft adjacent a surface of a body structure within the body cavity; and a cutting element disposed within said lumen near said distal end;

wherein said shaft is movable between a first position, in which said shaft substantially covers said cutting element, and a second position, in which at least a portion of said cutting element is exposed beyond said open distal end of said shaft.

47. A surgical cutting instrument comprising:

a shaft configured for percutaneous insertion into a body cavity of a patient having a proximal end and a distal end;

a cutting element disposed near the distal end of the shaft;

a grasping mechanism coupled to the shaft which is configured to grasp an outer surface of a body structure within the body cavity to hold the body structure to or near the distal end of the shaft; and actuating means disposed near the proximal end of the shaft for positioning the cutting element in contact with the body structure within the body cavity for cutting the body structure when the shaft is held adjacent to or near the distal end of said shaft.

\* \* \* \* \*